United States Patent
Larsen et al.

Patent Number: 5,842,981
Date of Patent: Dec. 1, 1998

[54] DIRECT TO DIGITAL OXIMETER

[75] Inventors: Michael T. Larsen, Wauwatosa; James L. Reuss, Waukesha, both of Wis.

[73] Assignee: Criticare Systems, Inc., Waukesha, Wis.

[21] Appl. No.: 683,617

[22] Filed: Jul. 17, 1996

[51] Int. Cl.[6] .......................................................... A61B 5/00
[52] U.S. Cl. ............................................................. 600/323
[58] Field of Search .................................. 128/633, 664, 128/665; 356/39, 41; 600/323, 330, 336, 473, 476

[56] References Cited

U.S. PATENT DOCUMENTS

| | | |
|---|---|---|
| 3,638,640 | 2/1972 | Shaw . |
| 3,799,672 | 3/1974 | Vurek . |
| 3,847,483 | 11/1974 | Shaw et al. . |
| 3,998,550 | 12/1976 | Konishi et al. . |
| 4,086,915 | 5/1978 | Kofsky et al. . |
| 4,167,331 | 9/1979 | Nielsen . |
| 4,266,554 | 5/1981 | Hamaguri . |
| 4,357,105 | 11/1982 | Loretz . |
| 4,407,290 | 10/1983 | Wilber . |
| 4,446,871 | 5/1984 | Imura . |
| 4,740,080 | 4/1988 | Donohue et al. ............................ 356/39 |
| 4,773,422 | 9/1988 | Isaacson et al. .......................... 128/633 |
| 4,807,631 | 2/1989 | Hersh et al. .............................. 128/633 |
| 4,854,699 | 8/1989 | Edgar, Jr. ................................. 128/633 |
| 5,190,038 | 3/1993 | Polson et al. ............................. 128/633 |
| 5,348,004 | 9/1994 | Hollub ...................................... 128/633 |
| 5,349,519 | 9/1994 | Kaestle .................................... 128/633 |
| 5,398,680 | 3/1995 | Folson et al. . |

*Primary Examiner*—Jennifer Bahr
*Assistant Examiner*—Eric F. Winakur
*Attorney, Agent, or Firm*—Reinhart, Boerner, Van Deuren, Norris & Rieselbach

[57] ABSTRACT

An oximeter for non-invasively measuring the oxygen saturation in blood with increased speed and accuracy. The device includes a sensor unit which can be attached to a patient and an oximeter which determines the oxygen saturation in the blood based on signals received from the sensor. In the present invention, the detected signal is immediately converted to a digital value.

15 Claims, 1 Drawing Sheet

DIRECT TO DIGITAL OXIMETER

The present invention is concerned generally with an improved oximeter for non-invasively measuring arterial oxygen saturation. More particularly, this invention is concerned with an improved method for direct digital signal formation from input signals produced by a sensor device which is connected to the oximeter.

In all oximeters, input signals are received from a sensor device which is directly connected to the blood-carrying tissue of a patient, such as a finger or ear lobe. The sensor device generally consists of a red LED, an infrared LED, and one or two photodetectors. Light from each LED is transmitted through the tissue, and the photodetectors detect the amount of light which passes through the tissue. The detected light consists of two components for each bandwidth. An AC component represents the amount of pulsating blood detected, while the DC component represents the amount of non-pulsating blood. Therefore, four separate components of detected light are examined in order to determine the arterial oxygen saturation: red DC, red AC, infrared DC and infrared AC. The amount of light detected is then used to determine the oxygen saturation in the blood of the patient based on the following equation:

(IR(AC)/IR(DC))/(Red(AC)/Red(DC))

In a traditional oximeter, the sensor output signal is converted to an analog voltage and then separated into infrared and red components. Some oximeters further separate the AC and DC components. Separate analog circuits are then used to sample, demultiplex, and filter these signals. In these systems, therefore, it is necessary to carefully match the analog components to minimize errors which can result from differences in gain or frequency response in the two circuits.

The instant invention improves on this method by receiving input current signals from at least two and preferably three LED's of different wavelengths and converting these input signals directly to digital voltage values, without first converting to analog voltages or separating the signals. This is accomplished by using a charge digitizing analog to digital converter with sufficient range to represent the large DC signals and sufficient resolution to represent the small AC signals. This charge digitizing converter employs a current integrator as the front stage, which tends to average and filter input noise. This is an improvement over the analog current to voltage conversion used in traditional oximeters, which tend to amplify noise.

Once the input current is converted to a digital voltage value, all input signals are processed along the same digital hardware path, instead of the separate analog hardware paths required by the traditional method. This system eliminates the need to match analog hardware components, and therefore further reduces potential errors. Furthermore, once the signals are digitized, a microprocessor can perform all of the signal processing, demultiplexing, and filtering steps required by traditional oximeters. This reduction in the analog signal processing stage increases both the speed and accuracy of the oximeter, decreases cost by eliminating expensive analog components, and reduces the size of the oximeter by eliminating physically large analog components.

It is therefore an object of this invention to provide an improved method for non-invasively measuring fluid parameters.

It is another object of this invention to provide an improved method for measuring arterial blood saturation.

It is another object of the invention to provide improved speed and accuracy in the measurements provided by oximeters.

It is another object of the invention to provide a direct analog to digital conversion of the input current signal with sufficient range to measure large DC signals and enough resolution to represent small AC signals so that accurate measurements can be made with reduced analog signal processing.

It is another object of the invention to provide a reduction in potential errors by directly converting the input current signal to a digital voltage signal, thereby bypassing the current to voltage conversion step which can amplify noise.

It is another object of the invention to provide a reduction in potential errors by processing all signals along one digital hardware path, thereby eliminating the need for matched analog components.

It is another object of the invention to provide an improved oximeter having a reduced number of electronic circuit components.

It is still another object of the invention to provide a reduction in the size of oximeters by eliminating physically large analog components.

It is yet a further object of the invention to provide an improved method and system for directly converting to digital signal form at least two signals from LED's of different wavelengths.

These and other object and advantages of the invention, together with the organization and manner of operation thereof, will become apparent from the following detailed description when taken in conjunction with the accompanying drawings described below.

DETAILED DESCRIPTION OF THE PREFERRED EMBODIMENT

Figure 1:
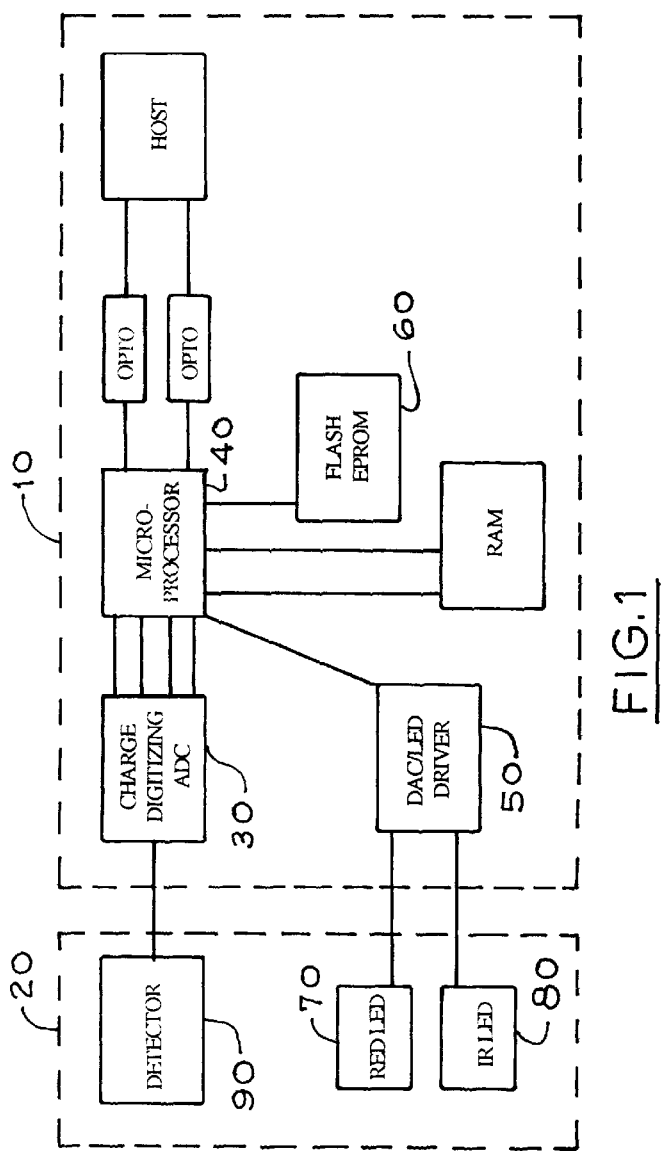
FIG. 1 illustrates a block diagram of the direct to digital oximeter as connected to a sensor device.

A block diagram of a direct to digital oximeter 10 constructed in accordance with the invention, along with an external sensor device 20 is shown in FIG. 1. The direct to digital oximeter 10 comprises a charge digitizing analog to digital converter 30, a microprocessor 40, a digital to analog converter/LED driver 50, and a flash EPROM 60. In order to achieve sufficient accuracy, the charge digitizing analog to digital converter 30 preferably converts the input analog signal to a digital signal of at least 20 bits.

Figure 2:
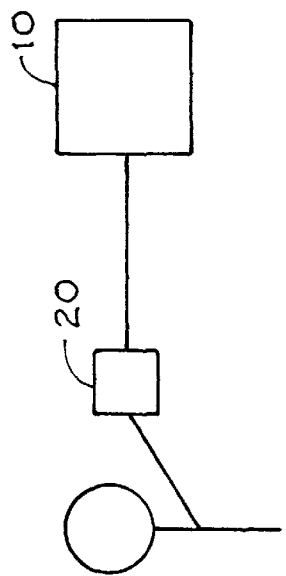
FIG. 2 illustrates the sensor device and direct to digital oximeter connected to a patient.

In a preferred embodiment (see FIG. 2) the sensor 20 is attached to a blood-carrying tissue sample, such as the finger or ear lobe of a patient. Here, the sensor 20 is shown to consist of a red LED 70, an infrared LED 80, and a single photodetector 90, but the sensor can include three or more LED's of different wavelengths and an associated plurality of photodetectors. The LED's 70 and 80 are driven by digital signals from the microprocessor 40. These digital signals are converted to analog voltages by means of the digital to analog converter/LED driver 50. Light from the LED's 70 and 80 is transmitted through the tissue sample, and is detected by the photodetector 90, which produces an analog current signal with an amplitude proportional to the amount of light detected in each bandwidth. The current signal from the photodetector 90 is then digitized with 20 bits of resolution by the charge digitizing analog to digital converter 30, and is sent to the microprocessor 40. Demultiplexing, ambient interference identification and elimination, and signal filtering are performed by means of digital signal processing software routines in the microprocessor 40. Once the signals are processed, the microprocessor 40 calculates the value of the ratio $$(IR(AC)/IR(DC))/(Red(AC)/Red(DC))$$

where the DC component represents the non-pulsating blood flow, and the AC component indicates the pulsatile blood flow. The microprocessor 40 then determines the absolute arterial oxygen saturation by comparing the result to the value stored in a look-up table in flash EPROM 60.

While preferred embodiments of the invention have been shown and described, it will be clear to those skilled in the art that various changes and modifications can be made without departing from the invention in its broader aspects as set forth in the claims provided hereinafter.

What is claimed is:

1. An oximeter for non-invasively measuring arterial oxygen saturation, comprising:
   a sensor including at least first and second light emitting devices for producing light in at least two wavelengths;
   at least one photodetector for detecting said light, after passing through a tissue sample containing a pulsating blood supply, and for producing an analog electrical current signal representing the absorption of each wavelength of said light;
   an analog to digital converter for converting said analog electrical current signal to a digital voltage signal; and
   a processing unit for processing said digital voltage signal to calculate an arterial oxygen saturation.

2. The oximeter of claim 1 wherein said sensor comprises LED's which produce light in three wavelengths.

3. The oximeter of claim 1 wherein said analog to digital converter comprises a charge digitizing analog to digital converter.

4. The oximeter of claim 1 wherein said analog to digital converter has sufficient range to measure large DC signals and sufficient resolution to represent small AC signals modulated on the DC signals.

5. The oximeter of claim 1 wherein said analog to digital converter includes a current integrator in the first stage.

6. The oximeter of claim 1 wherein said processing unit comprises a computer executing software routines.

7. The oximeter of claim 1 further comprising a stored look-up table for calculating oxygen saturation.

8. The oximeter of claim 1 further comprising a stored look-up table stored in flash EPROM for calculating oxygen saturation.

9. A method for non-invasively measuring arterial oxygen saturation, comprising the steps of:
   producing light of at least first and second wavelengths;
   directing said light at a tissue sample containing a pulsating blood supply;
   detecting said light, after passing through said tissue sample, and producing an analog electrical current signal representing the absorption rate of each wavelength of said light;
   then converting said analog electrical current signal to a digital voltage signal;
   then processing the digital voltage signal to calculate an arterial oxygen saturation.

10. The method as defined in claim 9 further including the step of utilizing a stored look-up table to calculate the oxygen saturation.

11. The method as defined in claim 9 further including the steps of storing a look-up table in a flash EPROM and utilizing this look-up table to calculate the oxygen saturation.

12. The method as defined in claim 9 further including the steps of identifying and filtering ambient noise from the digital voltage signal.

13. The method as defined in claim 9 further including the step of mathematically integrating the analog electrical current signal before converting said current signal to said input digital voltage.

14. The method as defined in claim 9 further including the step of demultiplexing the digital voltage signal to provide a first value representative of light detected of the first wavelength and a second value representative of light detected of the second wavelength.

15. The method as defined in claim 14 further including the step of digitally filtering the first and second values.

* * * * *